(12) United States Patent
Jacobsen et al.

(10) Patent No.: US 8,969,400 B2
(45) Date of Patent: Mar. 3, 2015

(54) PHARMACEUTICAL COMPOSITIONS OF 5-HYDROXYTRYPTOPHAN AND SEROTONIN-ENHANCING COMPOUND

(75) Inventors: Jacob Pade Ramsoe Jacobsen, Durham, NC (US); Brian Frøstrup, Lyngby (DK)

(73) Assignee: Duke University, Durham, NC (US)

( * ) Notice: Subject to any disclaimer, the term of this patent is extended or adjusted under 35 U.S.C. 154(b) by 573 days.

(21) Appl. No.: 12/680,843

(22) PCT Filed: Sep. 29, 2008

(86) PCT No.: PCT/EP2008/063012
§ 371 (c)(1),
(2), (4) Date: Jul. 20, 2010

(87) PCT Pub. No.: WO2009/043834
PCT Pub. Date: Apr. 9, 2009

(65) Prior Publication Data
US 2010/0298379 A1    Nov. 25, 2010

Related U.S. Application Data

(60) Provisional application No. 60/976,556, filed on Oct. 1, 2007.

(30) Foreign Application Priority Data

Oct. 1, 2007  (DK) .................................. 2007 01414

(51) Int. Cl.
| | | |
|---|---|---|
| *A01N 43/38* | (2006.01) | |
| *A61K 31/40* | (2006.01) | |
| *A61K 31/343* | (2006.01) | |
| *A61K 31/135* | (2006.01) | |
| *A61K 31/138* | (2006.01) | |
| *A61K 31/15* | (2006.01) | |
| *A61K 31/405* | (2006.01) | |
| *A61K 31/4525* | (2006.01) | |
| *A61K 45/06* | (2006.01) | |

(52) U.S. Cl.
CPC ............. *A61K 31/343* (2013.01); *A61K 31/135* (2013.01); *A61K 31/138* (2013.01); *A61K 31/15* (2013.01); *A61K 31/405* (2013.01); *A61K 31/4525* (2013.01); *A61K 45/06* (2013.01)
USPC ....................................................... 514/419

(58) Field of Classification Search
USPC ........................................................ 514/419
See application file for complete search history.

(56) References Cited

U.S. PATENT DOCUMENTS

| 7,517,908 B2 | 4/2009 | Krishnan et al. | |
| 7,585,627 B2 | 9/2009 | Caron et al. | |
| 2007/0117844 A1 * | 5/2007 | Morillo et al. | ................. 514/317 |
| 2007/0213370 A1 | 9/2007 | Morillo et al. | |
| 2009/0192166 A1 | 7/2009 | Krishnan et al. | |
| 2010/0256116 A1 | 10/2010 | Caron et al. | |

FOREIGN PATENT DOCUMENTS

| EP | 1637185 A1 | 3/2006 |
| WO | WO-2005/112906 A2 | 12/2005 |
| WO | WO 2012/054815 A1 | 4/2012 |

OTHER PUBLICATIONS

Scahill et al. "Fluoxetine Has No Marked Effect on Tic Symptoms in Patients with Tourette's Syndrome: A Double-Blind Placebo-Controlled Study" Journal of Child and Adolescent Psychopharmacology, 1997, vol. 7, No. 2, pp. 75-85.*
Wong et al. "Prozac (Fluoxetine, Lilly 110140), The First Selective Serotonin Uptake Inhibitor and an Antidepressant Drug: Twenty Years Since Its First Publication" Life Sciences, 1995, vol. 57, No. 5, pp. 411-441.*
Grabowski et al. "Fluoxetine Is Ineffective for Treatment of Cocaine Dependence or Concurrent Opiate and Cocaine Depencence: Two Placebo-Controlled, Double-Blind Trials" Journal of Clinical Psychopharmacology, 1995, vol. 15, pp. 163-174.*
Perry et al. "Extracellular 5-hydroxytryptamine concentration in rat hypothalamus after administration of fluoxetine plus L-5-hydroxytryptophan" J. Pharm. Pharmacol, 1993, vol. 45, No. 759-761.*
Sansom, L.N. "Oral extended-release products" Aust Prescr, 1999, vol. 22, pp. 88-90.*
Hans et al. "Biodegradable nanoparticles for drug delivery and targeting" Current Opinion in Solid State and Materials Science, 2002, pp. 319-327.*
Jacob P R Jacobsen et al: "Insensitivity of NMRI mice to selective serotonin reuptake inhibitors in the tail suspension test can be reversed by co-treatment with 5-hydroxytryptophan", Psychopharmacology, Springer, Berlin, DE, vol. 199, No. 2, May 22, 2008, pp. 137-150, XP019621086, ISSN: 1432-2072.
Turner et al: "Serotonin a la carte: Supplementation with the serotonin precursor 5-hydroxytryptophan", Pharmacology and Therapeutics, Elsevier, GB, vol. 109, No. 3, Mar. 1, 2006, pp. 325-338, XP005262786, ISSN: 0163-7258.
Jacobsen et al: "Differential sensitivity to SSRIs in the tail suspension test in NMRI and C57 mice: Relation to brain 5HT levels." European Neuropsyhcopharmacology: The Journal of the Eur. College of Neuropsychopharmacology vol. 17, Suppl 4, p. S375, (2007).
Van Praag, HM et al. 5-hydroxytryptophan in combination with clomipramine in "therapy-resistant" depressions. Psychopharmacologia (Berl.).1974; 38: 267-269.
Alino; JJL-I et al. 5-hydroxytryptophan (5-HTP) and a MAOI (nialamide)in the treatment of depressions. Int. Pharmacophychiat. 1976; 11: 8-15.

(Continued)

*Primary Examiner* — Kendra D Carter
(74) *Attorney, Agent, or Firm* — Myers Bigel Sibley & Sajovec, P.A.

(57) ABSTRACT

This invention relates to novel pharmaceutical compositions comprising a therapeutically effective amount of a slow-release formulation of 5-hydroxytryptophan (5-HTP) and a serotonin-enhancing compound. The pharmaceutical compositions for use according to the invention are contemplated particularly useful for combating CNS disorders, including depressive disorders, bipolar disorders, anxiety disorders, obesity and pain.

18 Claims, 4 Drawing Sheets

(56) References Cited

OTHER PUBLICATIONS

Van Hiele LJ. l-5-hydroxytryptophan in depression: the first substitution therapy in psychiatry? Neuropsychobiology. 1980; 6: 230-240.
Van Praag HM. Serotonin precursors in the treatment of depression. Advances in Biochemical Psychopharmacology. 1982:; 34: 259-286.
Nardini M et al. Treatment of depression with L-5-hydroxytryptophan combined with chorimipramine, a double-blind study. Int. J. Clin. Pharm. Res. 1983; III(4): 239-250.
Turner EH et al. Serotonin a la carte: supplementation with the serotonin precursor 5-hydroxytryptophan. Pharmacology & Therapeutics. 2006; 109: 325-338.
5HTP: MedlinePlus Supplements. U.S. National Library of Medication, *NIH* National Institutes of Health. http://www.nlm.nih.gov/medlineplus/druginfo/natural/794.html. 4 pages, retrieved Aug. 25, 2012.
Shaw K et al. Tryptophan and 5-hydroxytryptophan for depression. Cochrane Database Syst Rev. 2002;(1):CD003198. http://www.ncbi.nlm.nih.gov/pubmed/11869656. 2 pages, retrieved Jan. 17, 2013.
Thombre AG. Assessment of the feasibility of oral controlled release in an exploratory development setting. Drug Discovery Today. Sep. 2005; 10(17): 1159-1166.
Maderuelo C et al. Critical factors in the release of drugs from sustained release hydrophilic matrices. Journal of Controlled Release. 2011; 154: 2-19.
Livestrong.com. How to combine 5-HTP and SSRI. www.livestrong.com/article/425239-how-to-combine-5-htp-ssri. 4 pages; retrieved Jun. 27, 2013.
Livestrong.com. Can you take SSRIs and 5-HTP together? www.livestrong.com/article/455433-can-you-take-ssris-5-htp-together. 4 pages, retrieved Jun. 27, 2013.
Van Praag HM et al. 5-Hydroxytryptophan in combination with clomipramine in "therapy-resistant" depressions. Psychopharmacologia (Berl.). 1974; 38: 267-269.
Poewe WH et al. Treatment of motor fluctuations in Parkinson's disease with an oral sustained-release preparation of L-dopa: clinical and pharmacokinetic observations. Clinical Neuropharmacology. 1986; 9(5): 430-439.
Martin TG. Review, Serotonin syndrome. Annals of Emergency Medicine; Nov. 1996; 28(5): 520-526.
Verman RK et al. Formulation aspects in the development of osmotically controlled oral drug delivery systems. Journal of Controlled Release. 2002: 29: 7-27.
Thrombre AG et al. Osmotic drug delivery using swellable-core technology. Journal of Controlled Release. 2004; 94: 75-89.
Waterman KC et al. Osmotic capsules: a universal oral, controlled-release drug delivery dosage form. Journal of Controlled Release. 2011; 152: 264-269.
TOXNET Toxicology Data Network. 5-Hydroxytryptophan. CASRN: National Library of Medicine HSDB Database. 56-69-9: 17 pages. Retrieved Dec. 23, 2014. 17 pp.
MedlinePlus: 5-HTTP: Medline plus supplements. U.S. National Library of Medicine, NIH National Institutes of Health. 4 pages. Retrieved Dec. 23, 2013.
Adeyeye CM, Price JC (1994) Development and evaluation of sustained-release ibuprofen-wax microspheres. II. In vitro dissolution studies. Pharm Res 11: 575-9.
Amrol D (2007) Single-dose azithromycin microsphere formulation: a novel delivery system for antibiotics. International journal of nanomedicine 2: 9-12.
Beaulieu JM, Zhang X, Rodriguiz RM, Sotnikova TD, Cools MJ, Wetsel WC, Gainetdinov RR, Caron MG (2008) Role of GSK3 beta in behavioral abnormalities induced by serotonin deficiency. Proceedings of the National Academy of Sciences of the United States of America 105: 1333-8.
Blier P, El Mansari M (2013) Serotonin and beyond: therapeutics for major depression. Philos Trans R Soc Lond B Biol Sci 368: 20120536.
Brochet D, Martin P, Soubrie P, Simon P (1985) Effects of triiodothyronine on the 5-hydroxytryptophan-induced head twitch and its potentiation by antidepressants in mice. European journal of pharmacology 112: 411-4.

Byerley WF, Judd LL, Reimherr FW, Grosser BI (1987) 5-Hydroxytryptophan: a review of its antidepressant efficacy and adverse effects. J Clin Psychopharmacol 7: 127-37.
Carlson LA (2004) Niaspan, the prolonged release preparation of nicotinic acid (niacin), the broad-spectrum lipid drug. International journal of clinical practice 58: 706-13.
Conley R, Gupta SK, Sathyan G (2006) Clinical spectrum of the osmotic-controlled release oral delivery system (OROS), an advanced oral delivery form. Current medical research and opinion 22: 1879-92.
Delgado PL (2006) Monoamine depletion studies: implications for antidepressant discontinuation syndrome. J Clin Psychiatry 67 Suppl 4: 22-6.
Delgado PL, Charney DS, Price LH, Aghajanian GK, Landis H, Heninger GR (1990) Serotonin function and the mechanism of antidepressant action. Reversal of antidepressant-induced remission by rapid depletion of plasma tryptophan. Arch Gen Psychiatry 47: 411-8.
Ebert D, Albert R, May A, Stosiek I, Kaschka W (1995) Combined SSRI-RIMA treatment in refractory depression. Safety data and efficacy. Psychopharmacology 119: 342-4.
Fuxe K, Ogren SO, Agnati LF, Andersson K, Eneroth P (1982) Effects of subchronic antidepressant drug treatment on central serotonergic mechanisms in the male rat. Adv Biochem Psychopharmacol 31: 91-107.
Gallardo D, Skalsky B, Kleinebudde P (2008) Controlled release solid dosage forms using combinations of (meth)acrylate copolymers. Pharmaceutical development and technology 13: 413-23.
Gijsman HJ, van Gerven JM, de Kam ML, Schoemaker RC, Pieters MS, Weemaes M, de Rijk R, van der Post J, Cohen AF (2002) Placebo-controlled comparison of three dose-regimens of 5-hydroxytryptophan challenge test in healthy volunteers. J Clin Psychopharmacol 22: 183-9.
Haddad PM (2001) Antidepressant discontinuation syndromes. Drug Saf 24: 183-97.
Iovieno N, Dalton ED, Fava M, Mischoulon D (2011) Second-tier natural antidepressants: review and critique. Journal of affective disorders 130: 343-57.
Jacobsen JP, Medvedev IO, Caron MG (2012a) The 5-HT deficiency theory of depression: perspectives from a naturalistic 5-HT deficiency model, the tryptophan hydroxylase 2Arg439His knockin mouse. Philos Trans R Soc Lond B Biol Sci 367: 2444-59.
Jacobsen JP, Siesser WB, Sachs BD, Peterson S, Cools MJ, Setola V, Folgering JH, Flik G, Caron MG (2012b) Deficient serotonin neurotransmission and depression-like serotonin biomarker alterations in tryptophan hydroxylase 2 (Tph2) loss-of-function mice. Molecular psychiatry 17: 694-704.
Levine AM, Burdick RK (2005) Controlled-release oxycodone. The Journal of the American Academy of Orthopaedic Surgeons 13: 1-4.
Levine J, Schooler NR (1986) SAFTEE: a technique for the systematic assessment of side effects in clinical trials. Psychopharmacology bulletin 22: 343-81.
Sanchez C, Bergqvist PB, Brennum LT, Gupta S, Hogg S, Larsen A, Wiborg O (2003) Escitalopram, the S-(+)-enantiomer of citalopram, is a selective serotonin reuptake inhibitor with potent effects in animal models predictive of antidepressant and anxiolytic activities. Psychopharmacology 167: 353-62.
Steele M, Weiss M, Swanson J, Wang J, Prinzo RS, Binder CE (2006) A randomized, controlled effectiveness trial of OROS-methylphenidate compared to usual care with immediate-release methylphenidate in attention deficit-hyperactivity disorder. Can J Clin Pharmacol 13: e50-62.
Trimble MR (1990) Worldwide use of clomipramine. J Clin Psychiatry 51 Suppl: 51-4; discussion 55-8.
Wellington K, Perry CM (2001) Venlafaxine extended-release: a review of its use in the management of major depression. CNS drugs 15: 643-69.

\* cited by examiner

PHARMACEUTICAL COMPOSITIONS OF 5-HYDROXYTRYPTOPHAN AND SEROTONIN-ENHANCING COMPOUND

TECHNICAL FIELD

This invention relates to novel pharmaceutical compositions comprising a therapeutically effective amount of a slow-release formulation of 5-hydroxytryptophan (5-HTP) and a serotonin-enhancing compound. The pharmaceutical compositions for use according to the invention are contemplated particularly useful for combating CNS disorders, including depressive disorders, bipolar disorders, anxiety disorders, obesity and pain.

BACKGROUND ART

Drugs that inhibit the serotonin transporter, such as Selective Serotonin Reuptake Inhibitors (SSRIs), Serotonin-Noradrenaline Reuptake Inhibitors (SNRIs) and certain members of the Tricyclic Antidepressant (TCA) class of drugs, currently provide efficacy in the treatment of several CNS disorders, including depressive and anxiety disorders. SSRIs and SNRIs are generally perceived by psychiatrists and primary care physicians as effective, well-tolerated and easily administered.

However, with the high incidence of non- and insufficient responders to serotonin enhancing drugs treatment there is impetus for developing adjunct therapies that could enhance the efficacy of these drugs in treatments of CNS disorders, including depressive disorders, bipolar disorders and anxiety disorders.

5-HTP is the immediate precursor of serotonin. 5-HTP as monotherapy is reported to have some clinical efficacy in depression. However, the short half-life of 5-HTP, 4 hours, limits the utility of immediate-release formulations of 5-HTP due to large fluctuations in plasma levels, multiple daily doses necessary and/or possibility of nocturnal subtherapuetic plasma levels. 5-HTP treatment in standard, immediate-release formulations has been associated with gastrointestinal adverse events in some patients.

The use of 5-HTP in combination therapy to serotonin transporter inhibitor treatment of depression has been suggested in the prior art (reviewed in Turner E H, Loftis J M and Blackwell A D. "Serotonin a la carte: supplementation with the serotonin precursor 5-hydroxytryptophan". Pharmacol Ther. 2006 109(3); 325-38).

However, the relatively short half-life of 5-HTP (about 4 hours) means that dosing needs to be frequent in order maintain a steady plasma level, which inevitably leads to large fluctuations in systemic 5-HTP available for conversion to 5-HT and an inconsistent pharmacodynamic effect. Further, fluctuations in 5-HT levels in patients sustained on SSRIs are associated with mood-fluctuations, Moreover, side effects such as nausea and vomiting associated with 5-HTP treatment are most commonly seen shortly after dosing at a time when systemic 5-HTP levels are peaking, Further, in case of overdosing there is a risk of adverse events—such as serotonin syndrome.

EP 1 627 185 A1 relates to controlled-release formulations containing tryptophan and/or its metabolites.

SUMMARY OF THE INVENTION

Investigations carried out by the inventor have lead to the conclusion that a combination of a slow-release formulation of 5-hydroxytryptophan and a serotonin-enhancing compound constitutes a particularly useful combination for use in therapy associated with CNS disorders.

5-HTP can increase brain levels of serotonin and thereby increase the availability of serotonin for release by serotonin-enhancing compounds.

In its first aspect the invention provides a pharmaceutical composition comprising a therapeutically effective amount of a slow-release formulation of 5-hydroxytryptophan or a pharmaceutically acceptable salt thereof and a serotonin-enhancing compound or a pharmaceutically acceptable salt thereof, together with one or more adjuvants, excipients, carriers and/or diluents.

In another aspect the invention relates to the use of a slow-release formulation of 5-hydroxytryptophan or a pharmaceutically acceptable salt thereof and a serotonin-enhancing compound or a pharmaceutically acceptable salt thereof, for the manufacture of a medicament for the treatment, prevention or alleviation of CNS disorders of a mammal, including a human.

In a third aspect the invention provides a kit of parts comprising at least two separate unit dosage forms (A) and (B), wherein (A) comprises a slow-release formulation of 5-hydroxytryptophan or a pharmaceutically acceptable salt thereof; and (B) comprises a serotonin-enhancing compound or a pharmaceutically acceptable salt thereof; and optionally (C) instructions for the simultaneous, sequential or separate administration of the slow-release formulation of 5-hydroxytryptophan of (A) and the serotonin-enhancing compound of (B) to a patient in need thereof.

In a final aspect the invention provides a method of treatment, prevention or alleviation of CNS disorders of a living animal body, including a human, which method comprises the step of administering to such a living animal body in need thereof, a therapeutically effective amount of a compound of formula I, any of its isomers or any mixture of its isomers, or a pharmaceutically acceptable salt thereof; and a serotonin-enhancing compound or a pharmaceutically acceptable salt thereof.

Other objects of the invention will be apparent to the person skilled in the art from the following detailed description and examples.

DETAILED DISCLOSURE OF THE INVENTION

In its first aspect the invention provides a pharmaceutical composition comprising a therapeutically effective amount of
(i) a slow-release formulation of 5-hydroxytryptophan or a pharmaceutically acceptable salt thereof; and
(ii) a serotonin-enhancing compound;
or a pharmaceutically acceptable salt thereof;
together with one or more adjuvants, excipients, carriers and/or diluents.

A Slow-Release Formulation of 5-hydroxytryptophan

Slow-release formulations of 5-hydroxytryptophan, such as slow-release formulations of L-5-hydroxytryptophan, may be prepared by formulation methods known in the art, such as in the latest edition of *Controlled drug delivery* (Drugs and the pharmaceutical sciences; vol. 29; Marcel Dekker, Inc) and the latest edition of *Modified-Release Drug Delivery Technology* (Drugs and the pharmaceutical sciences; vol. 126; Marcel Dekker, Inc). The route of administration of the slow-release formulation may preferably include oral administration, in particular in tablet, in capsule, in dragé, in powder, or in liquid form, and parenteral administration, in particular cutaneous, subcutaneous, intramuscular, or intravenous injection.

In one embodiment the slow-release formulation of 5-hydroxytryptophan has a half-life of from 8 to 48 hours. In a further embodiment, the slow-release formulation of 5-hydroxytryptophan has a half-life of from 12 to 48 hours. In a still further embodiment, the slow-release formulation of 5-hydroxytryptophan has a half-life of from 24 to 48 hours.

Serotonin-Enhancing Compounds

The serotonin-enhancing compounds for use according to the invention are known in the art and may be commercially available under different brand names, or may be obtained as described in the literature.

Examples of serotonin-enhancing compounds are selective serotonin reuptake inhibitors (SSRIs), serotonin-norepinephrine reuptake inhibitors (SNRIs), tricyclic antidepressants (TCAs), and monoamine oxidase inhibitors (MAOIs).

In one embodiment, the serotonin-enhancing compound is selected from the group consisting of: citalopram, escitalopram, fluoxetine, fluvoxamine, paroxetine, sertraline, venlafaxine, duloxetine, moclobemide, tranylcypromine, and phenelzine.

In a further embodiment, the serotonin-enhancing compound is selected from the group of: citalopram, escitalopram, fluoxetine, fluvoxamine, paroxetine, sertraline, or a pharmaceutically acceptable salt thereof.

In a still further embodiment, the serotonin-enhancing compound is selected from the group of: citalopram, escitalopram, fluvoxamine, paroxetine, sertraline, or a pharmaceutically acceptable salt thereof.

In a special embodiment, the serotonin-enhancing compound is citalopram, escitalopram, or a pharmaceutically acceptable salt thereof.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, and the toluene-p-sulphonate salt, and the like. Such salts may be formed by procedures well known and described in the art.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

In a further embodiment, the pharmaceutically acceptable salt of L-5-hydroxytryptophan is the sodium, the potassium, the calcium, the magnesium, the sulphate, the ammonium, the L-arginine, the choline, the lysine, the betaine, the diethylamine, the benzathine, the dimethylaminoethanol, the 1-(2-hydroxyethyl)-2-pyrrolidone, the triethanolamine, or the tromethamine salt of L-5-hydroxytryptophan.

In a special embodiment, the pharmaceutically acceptable salt of L-5-hydroxytryptophan is the sodium salt of L-5-hydroxytryptophan. In a further special embodiment, the pharmaceutically acceptable salt of L-5-hydroxytryptophan is the potassium salt of L-5-hydroxytryptophan. In a still further special embodiment, the pharmaceutically acceptable salt of L-5-hydroxytryptophan is the calcium salt of L-5-hydroxytryptophan, In a further special embodiment, the pharmaceutically acceptable salt of L-5-hydroxytryptophan is the magnesium salt of L-5-hydroxytryptophan. In a still further special embodiment, the pharmaceutically acceptable salt of L-5-hydroxytryptophan is the sulphate salt of L-5-hydroxytryptophan. In a further special embodiment, the pharmaceutically acceptable salt of L-5-hydroxytryptophan is the ammonium salt of L-5-hydroxytryptophan. In a still further special embodiment, the pharmaceutically acceptable salt of L-5-hydroxytryptophan is the L-arginine salt of L-5-hydroxytryptophan. In a further special embodiment, the pharmaceutically acceptable salt of L-5-hydroxytryptophan is the choline salt of L-5-hydroxytryptophan. In a still further special embodiment, the pharmaceutically acceptable salt of L-5-hydroxytryptophan is the lysine salt of L-5-hydroxytryptophan. In a further special embodiment, the pharmaceutically acceptable salt of L-5-hydroxytryptophan is the betaine salt of L-5-hydroxytryptophan. In a still further special embodiment, the pharmaceutically acceptable salt of L-5-hydroxytryptophan is the diethylamine salt of L-5-hydroxytryptophan. In a further special embodiment, the pharmaceutically acceptable salt of L-5-hydroxytryptophan is the benzathine salt of L-5-hydroxytryptophan. In a still further special embodiment, the pharmaceutically acceptable salt of L-5-hydroxytryptophan is the dimethylaminoethanol salt of L-5-hydroxytryptophan. In a further special embodiment, the pharmaceutically acceptable salt of L-5-hydroxytryptophan is the 1-(2-hydroxyethyl)-2-pyrrolidone salt of L-5-hydroxytryptophan. In a still further special embodiment, the pharmaceutically acceptable salt of L-5-hydroxytryptophan is the triethanolamine salt of L-5-hydroxytryptophan. In a further special embodiment, the pharmaceutically acceptable salt of L-5-hydroxytryptophan is the tromethamine salt of L-5-hydroxytryptophan.

In a further embodiment, the pharmaceutically acceptable salt of L-5-hydroxytryptophan is the acetate, the carbonate, the glycolate, the D-lactate, the L-lactate, the phosphate, the bromide, the D-mandelate, the L-mandelate, the thiocyanate, the maleate, the L-malate, the glutarate, the succinate, the isobutarate, the oxalate, the propinoate, the nicotinate, the malonate, or the xinafoate salt of 5-hydroxytryptophan.

In a special embodiment, the pharmaceutically acceptable salt of L-5-hydroxytryptophan is the acetate salt of L-5-hydroxytryptophan. In a further special embodiment, the pharmaceutically acceptable salt of L-5-hydroxytryptophan is the carbonate salt of L-5-hydroxytryptophan. In a still further special embodiment, the pharmaceutically acceptable salt of L-5-hydroxytryptophan is the glycolate salt of L-5-hydroxytryptophan. In a further special embodiment, the pharmaceutically acceptable salt of L-5-hydroxytryptophan is the D-lactate salt of L-5-hydroxytryptophan. In a still further special embodiment, the pharmaceutically acceptable salt of L-5-hydroxytryptophan is the L-lactate salt of L-5-hydroxytryptophan. In a further special embodiment, the pharmaceutically acceptable salt of L-5-hydroxytryptophan is the phosphate salt of L-5-hydroxytryptophan. In a still further special embodiment, the pharmaceutically acceptable salt of L-5-hydroxytryptophan is the bromide salt of L-5-hydroxytryptophan. In a further special embodiment, the pharmaceutically acceptable salt of L-5-hydroxytryptophan is the D-mandelate salt of L-5-hydroxytryptophan. In a still further special embodiment, the pharmaceutically acceptable salt of L-5-hydroxytryptophan is the L-mandelate salt of L-5-hydroxytryptophan. In a further special embodiment, the pharmaceutically acceptable salt of L-5-hydroxytryptophan is the thiocyanate salt of L-5-hydroxytryptophan. In a still further special embodiment, the pharmaceutically acceptable salt of L-5-hydroxytryptophan is the maleate salt of L-5-hydroxytryptophan. In a further special embodiment, the pharmaceutically acceptable salt of L-5-hydroxytryptophan is the L-malate salt of L-5-hydroxytryptophan. In a still further special embodiment, the pharmaceutically acceptable salt of L-5-hydroxytryptophan is the glutarate salt of L-5-hydroxytryptophan. In a further special embodiment, the pharmaceutically acceptable salt of L-5-hydroxytryptophan is the succinate salt of L-5-hydroxytryptophan. In a still further special embodiment, the pharmaceutically acceptable salt of L-5-hydroxytryptophan is the isobutarate salt of L-5-hydroxytryptophan, In a further special embodiment, the pharmaceutically acceptable salt of L-5-hydroxytryptophan is the oxalate salt of L-5-hydroxytryptophan. In a still further special embodiment, the pharmaceutically acceptable salt of L-5-hydroxytryptophan is the propinoate salt of L-5-hydroxytryptophan. In a further special embodiment, the pharmaceutically acceptable salt of L-5-hydroxytryptophan is the nicotinate salt of L-5-hydroxytryptophan. In a still further special embodiment, the pharmaceutically acceptable salt of L-5-hydroxytryptophan is the malonate salt of L-5-hydroxytryptophan. In a further special embodiment, the pharmaceutically acceptable salt of L-5-hydroxytryptophan is the xinafoate salt of L-5-hydroxytryptophan.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Biological Activity

The pharmaceutical compositions for use according to the invention are contemplated particularly useful for combating CNS disorders.

In one embodiment the CNS disorder is a disorder or condition selected from the group consisting of depressive disorders, bipolar disorders, anxiety disorders, psychotic disorders, obesity, pain and drug addiction. In a special embodiment the CNS disorder is a disorder or condition selected from the group consisting of depression, interferon-induced depression, and depression resistant to re-uptake inhibitors.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In a preferred embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage of each of the active ingredients depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

Each of the active ingredients may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Pharmaceutical Kits of Parts

According to the invention there is also provided a kit of parts comprising at least two separate unit dosage forms (A) and (B):

(A) a slow-release formulation of 5-hydroxytryptophan or a pharmaceutically acceptable salt thereof; and
(B) a serotonin-enhancing compound;
or a pharmaceutically acceptable salt thereof; and optionally
(C) instructions for the simultaneous, sequential or separate administration of 5-hydroxytryptophan of (A) and the serotonin-enhancing compound of (B) to a patient in need thereof.

The slow-release formulation of 5-hydroxytryptophan for use according to the invention and the serotonin-enhancing compound for use according to the invention may preferably be provided in a form that is suitable for administration in conjunction with the other. This is intended to include instances where one or the other of two formulations may be administered (optionally repeatedly) prior to, after, and/or at the same time as administration with the other component.

Also, the slow-release formulation of 5-hydroxytryptophan for use according to the invention and the serotonin-enhancing compound for use according to the invention may be administered in a combined form, or separately or separately and sequentially, wherein the sequential administration is close in time or remote in time. This may in particular include that two formulations are administered (optionally repeatedly) sufficiently closely in time for there to be a beneficial effect for the patient, that is greater over the course of the treatment of the relevant condition than if either of the two formulations are administered (optionally repeatedly) alone, in the absence of the other formulation, over the same course of treatment. Determination of whether a combination provides a greater beneficial effect in respect of, and over the course of treatment of, a particular condition, will depend upon the condition to be treated or prevented, but may be achieved routinely by the person skilled in the art.

When used in this context, the terms "administered simultaneously" and "administered at the same time as" include that individual doses of the slow-release formulation of 5-hydroxytryptophan or a pharmaceutically acceptable salt thereof and the serotonin-enhancing compound or a pharmaceutically acceptable salt thereof are administered within 48 hours, e.g. 24 hours, of each other.

Bringing the two components into association with each other, includes that components (A) and (B) may be provided as separate formulations (i.e. independently of one another), which are subsequently brought together for use in conjunction with each other in combination therapy; or packaged and presented together as separate components of a "combination pack" for use in conjunction with each other in combination therapy.

Methods of Therapy

In another aspect the invention provides methods of treatment, prevention or alleviation of a CNS disorder of a living animal body, including a human, which method comprises the step of administering to such a living animal body in need thereof, a therapeutically effective amount of a combination of a slow-release formulation of 5-hydroxytryptophan or a pharmaceutically acceptable salt thereof; and a serotonin-enhancing compound or a pharmaceutically acceptable salt thereof.

The preferred indications contemplated according to the invention are those stated above.

It is at present contemplated that suitable dosage ranges—for each of the active compounds—are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge. When administered in combination with further compounds known in the art for treatment of the diseases, the dosage regimen may be reduced.

BRIEF DESCRIPTION OF THE DRAWINGS

The present invention is further illustrated by reference to the accompanying drawing, in which.

EXAMPLES

The invention is further illustrated with reference to the following examples, which are not intended to be in any way limiting to the scope of the invention as claimed.

Introduction

Figure 1:
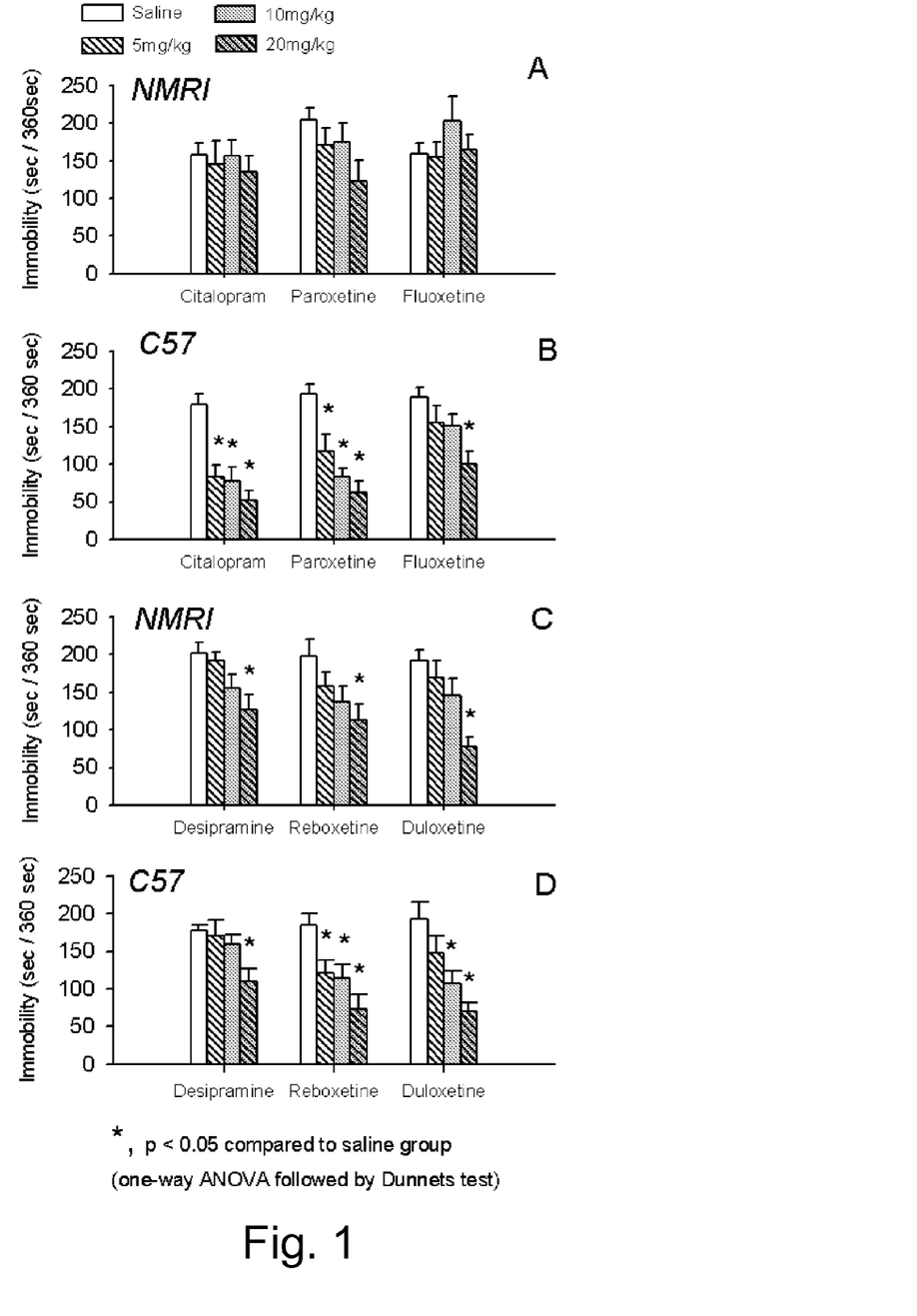
FIG. 1 shows that in the tail suspension test of antidepressant action NMRI mice are unresponsive to SSRIs while C57Bl/6j mice respond to SSRIs.

Drug candidates can be screened for antidepressant-like activity by using animal models. In the tail suspension test the mouse is suspended by its tail. The mouse will initially move and struggle but will with time become increasingly immobile. Pretreatment with a clinically effective antidepressant decreases the time spent immobile. This includes selective serotonin re-uptake inhibitors (SSRIs) and drugs inhibiting the noradrenaline reuptake mechanism, as well as some putative antidepressants with non-monoamine pharmacology. The neurobiology of decreased immobility in mice is believed to parallel the neurobiology of antidepressant action in humans. In animal models of depression, including the tail suspension test, mouse strains differ considerably in their responsiveness to antidepressants. This may parallel the clinical situation where a considerable subset of patients is refractory to pharmacotherapy. Several lines of evidence suggests that impairments in the 5-hydroxytryptamine (5-HT) neurotransmitter system may dispose to depression and lack of response to 5-HTergic antidepressants in humans [6,13]. In our laboratory mice of the NMRI strain consistently fails to repond to SSRIs in the tail suspension test of antidepressant activity, while C57 mice show a strong response (FIG. 1).

The aim of the present study was two-fold: 1. To examine whether this interstrain difference in SSRI responsiveness was paralleled by different brain 5-HT levels. 2. To examine whether treatment with the 5-HT precursor 5-hydroxytryptophan (5-HTP) could increase brain 5-HT levels and confer SSRIs responsiveness in the tail suspension test in NMRI mice.

Methods

Animals

Male NMRI and C57Bl/6j mice (Taconic Europe, St. Laven, DK) weighing 25-35 g were housed and habituated for at least 7 days before the experiments in Macrolon III cages (20×40×18 cm) with eight mice per cage. Chow and water were available ad libitum, with lights on at 6 a.m. and off at 6 p.m. All behavioral testing was conducted during the light phase.

Drug Treatments

Fluoxetine HCl, desipramine HCL, 5-hydroxytryptamine, citalopram HBr, paroxetine HCl, reboxetine fumarate and duloxetine oxalate. All drugs were administered i.p. in saline in a volume of 10 ml/kg. In the tail suspension and locomotor activity experiments drugs were injected 30 min prior to test.

Tail Suspension Test

The tail suspension test employed was a modified version to that described elsewhere. Mice were suspended individually by the tail using adhesive tape (attached 2 cm from tip of the tail) to a hook attached to a strain gauge and left there for 6 min. The duration of immobility was measured using an automated system (Med Associates, USA) during the 6 min testing period.

Locomotor Activity

Locomotor activity following saline, saline/citalopram (5, 10 and 20 mg/kg), 5-HTP (12.5 mg/kg) and 5-HTP (12.5 mg/kg)/citalopram (5, 10 and 20 mg/kg) were recorded for 6 min using an automated system as described in Hansen H H et al.; Eur J Pharmacol 2007; 570:77-88.

Tissue Dissesctions

Mice killed by cervical dislocation and the frontal cortex and hippocampus rapidly dissected, frozen on dry ice and stored at −80° C. until analysis by HPLC-EC.

Microdialysis

Microdialysis were performed in freely moving mice as previously described in Jacobsen J P et al.; Neuroscience 2005; 132:1055-1072. The flowrate was 1 ul/min and 20 min samples were collected. Four baseline samples were collected whereafter saline, 5-HTP (12.5 mg/kg), citalopram (20 mg/kg) or citalopram+5-HTP were injected and six additional samples where collected. Samples were collected on ice, immediatedly frozen on dry ice and stored at −80° C. until analysis by HPLC-EC.

5-HT Analysis

5-HT in tissue and microdialysis samples were analysed using HPLC-EC as previously described in Weikop P et al.; Eur Neuropsychopharmacol 2007; 17:658-671.

Statistics

Tail suspension data were analyzed either using one-way ANOVA (single-drug treatments) or two-way ANOVA (paroxetine/5-HTP and citalopram/5-HTP) with Dunnets post-hoc test. Locomotor activity data were analyzed using two-way ANOVA with Dunnets post-hoc test. Tissue 5-HT data were analyzed using students t-test. Microdialysis 5-HT data were analyzed using two-way repeated measures ANOVA with Dunnets post-hoc test.

Results

Effect of Antidepressants in Tail Suspension in NMRI and C57 Mice.

In NMRI mice only drugs with noradrenaline reuptake inhibitory activity (desipramine, reboxetine and duloxetine) reduced immobility (FIG. 1C), while SSRIs (paroxetine, citalopram and fluoxetine) were without effect (FIG. 1A). In contrast, both selective noradrenaline reuptake inihibitors (desipramine, reboxetine), serotonin-noradraneline reuptake inihibitors and SSRIs decreased immobility in C57 mice (FIGS. 1B, 1D).

Tissue Levels of 5-HT is Decreased in the Frontal Cortex and Hippocampus of NMRI Compared to C57 Mice This insensitivity to SSRIs in the tail suspension test of NMRI mice could be related to low brain levels of the substrate of SSRI action, 5-HT. Therefore we compared the levels of 5-HT in the frontal cortex and hippocampus, two regions involved in affective behavior, of NMRI and C57 mice. HPLC analysis demonstrated that 5-HT in the hippocampus and frontal cortex of C57 mice were about twice the levels in NMRI mice. The test results are shown in Table 1 below.

TABLE 1

Tissue 5-HT and 5-HIAA (% of NMRI) in frontal
cortex and hippocampus in NMRI and C57 mice.

|  | 5-HT levels ± sem |
|---|---|
| Frontal Cortex - NMRI | 100 ± 8 |
| Frontal Cortex - C57 | 182 ± 18 |
| Hippocampus - NMRI | 100 ± 22 |
| Hippocampus - C57 | 236 ± 12 |

5-HTP Increases Tissue 5-HT in the Frontal Cortex but not the Hippocampus

Next we examined whether acute administration of the 5-HT precursor 5-HTP could increase brain 5-HT in NMRI mice. In the frontal cortex 5-HTP increased 5-HT by 22%, while in the hippocampus a decrease of 17% was found. The test results are shown in Table 2 below.

TABLE 2

Effect of 5-HTP on brain 5-HT (% of saline) in NMRI mice.

|  | 5-HT levels ± sem |
|---|---|
| Frontal Cortex - Saline | 100 ± 2.8 |
| Frontal Cortex - 5-HT | 122 ± 3.3 |
| Hippocampus - Saline | 100 ± 5.5 |
| Hippocampus - 5-HT | 83.4 ± 2.6 |

Figure 2:
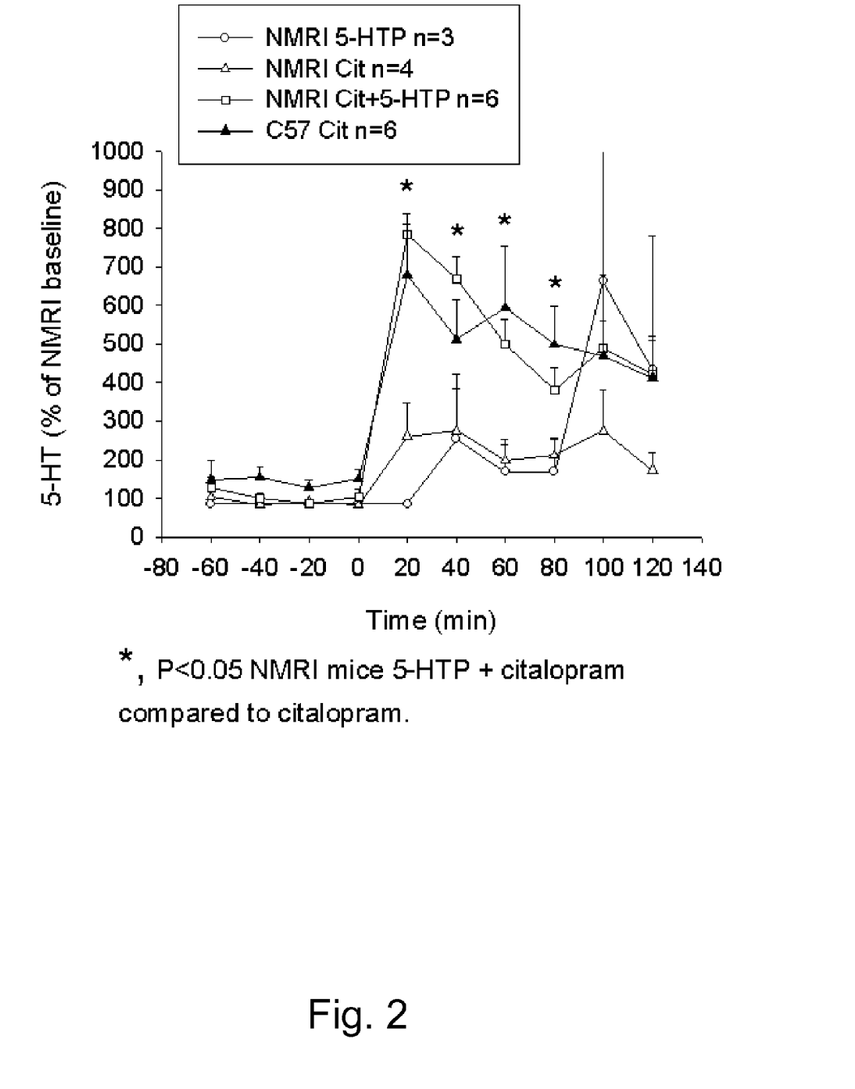
FIG. 2 shows that co-treatment with 5-HTP augments the increase in extracellular 5-HT following admistration of the SSRI citalopram in NMRI mice.

5-HTP Augments the Extracellular 5-HT Response to Citalopram in the Frontal Cortex Increased tissue levels of 5-HT in the frontal cortex following 5-HTP administration could indicate that more 5-HT were available for release. If so, the increase in extracelullar 5-HT after SSRI treatment could be augmented. To test this hypothesis we performed microdialysis in the frontal cortex. In NMRI mice only a modest increase in 5-HT was seen after administration of either citalopram (20 mg/kg) or 5-HTP (12.5 mg/kg) (FIG. 2). In C57 mice the baseline pre-injection 5-HT levels were significantly higher than in NMRI mice (data not shown). Following injection of citalopram in C57 mice a robust increase in 5-HT was found (FIG. 2). Co-injecting 5-HTP (12.5 mg/kg) with citalopram in NMRI mice resulted in a significantly higher 5-HT increase compared to when citalopram was injected alone (FIG. 2). These data demonstrates that 5-HT can increase 5-HT neurotransmission following administration of the SSRI citalopram, at least in the frontal cortex.

Figure 3:
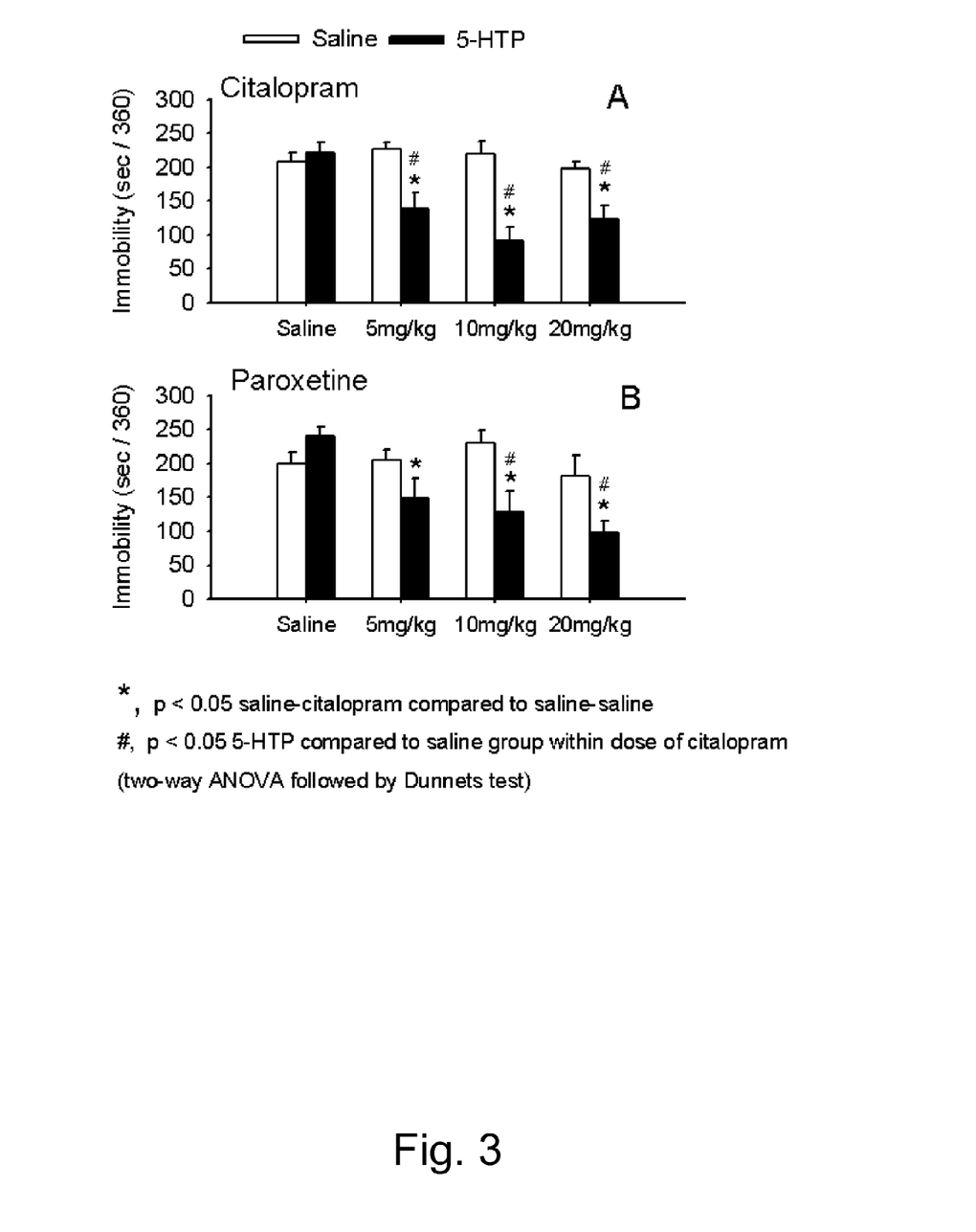
FIG. 3: shows that co-treatment with 5-HTP confers SSRI responsiveness in NMRI mice in the tail suspension test.

Co-Treatment with 5-HTP Restores the Antidepressant-Like Response to SSRIs in NMRI Mice Given the ability of 5-HTP to increase frontal cortex 5-HT and to enhance the extracellular levels of 5-HT following citalopram in NMRI mice, we hypothezised that 5-HTP could also restore the antidepressant-like response to SSRIs. Indeed, when 5-HTP (12.5 mg/kg) was co-administered with either citalopram or paroxetine a robust and dose dependent antidepressant-like response was found in NMRI mice (FIG. 3). 5-HTP alone did not affect immobility.

Figure 4:
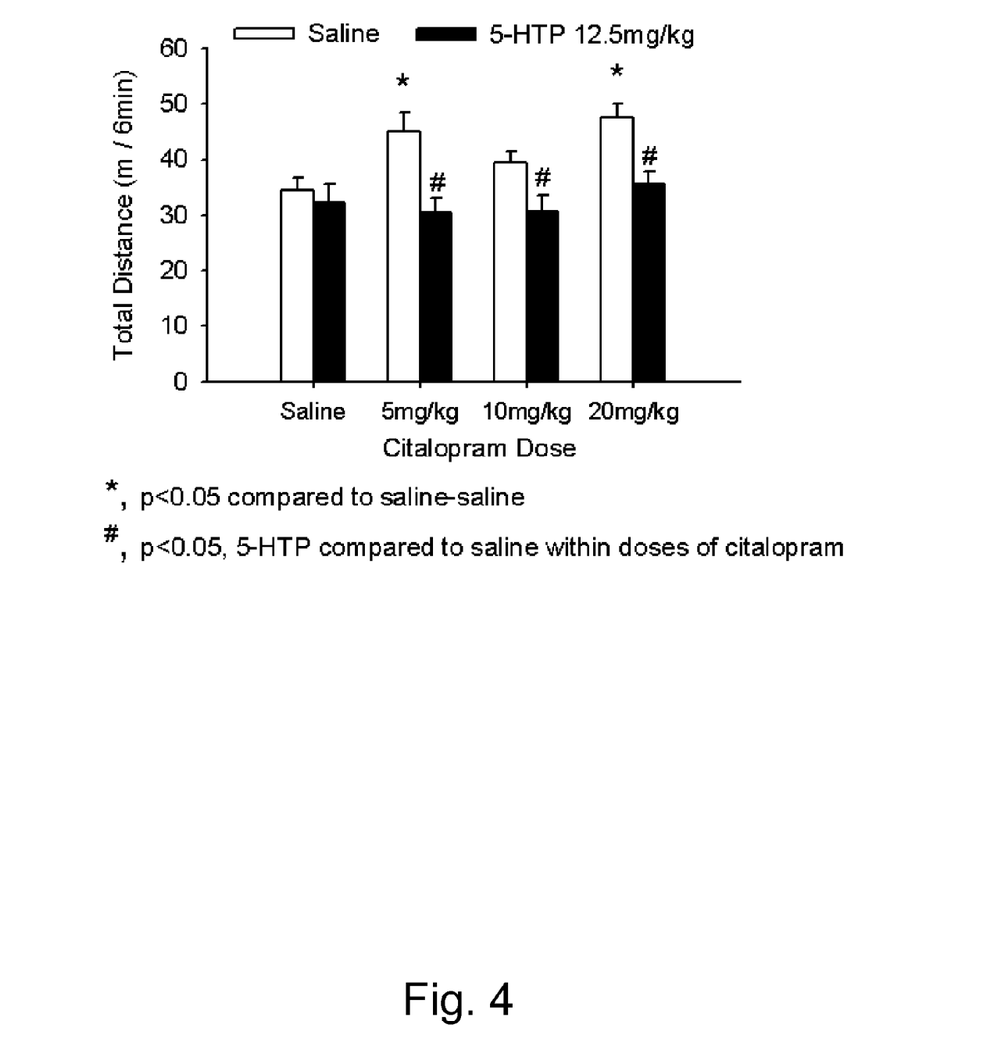
FIG. 4: shows that co-treatment of 5-HTP with citalopram does not increase locomotor activity.

Co-Treatment of Citalopram with 5-HTP does not Increase Locomotor Activity in NMRI Mice Drugs treatment having a general stimulatory influence on locomotor activity can strike out as false positives in the tail suspension test and similar test based on the animals activity level. However, some clinically effective antidepressants do affect locomotor activity, in a compound-specific fashion [9]. To determine whether general increase activity could be a potential confound, we tested the combination of 5-HTP and citalopram in locomotor chambers. Citalopram (5 and 20 mg/kg) alone moderately but significantly increased locomotor activity. In contrast, the combination of 5-HTP (12.5 mg/kg) and citalopram (5, 10 and 20 mg/kg) had no effect on locomotor activity (FIG. 4). Thus, it is unlikely that the antidepressant-like effect of co-treatment with 5-HTP and SSRIs in the tail suspension test in NMRI mice is confounded by a non-specific increase in general locomotor activity.

DISCUSSION

Here we demonstrate that 5-HTP confers sensitivity to SSRIs in otherwise SSRI-insensitive NMRI mice in the tail suspension test of antidepressant-like activity. The restoration of the behavioral response was paralleled by indices of increased 5-HT neurotransmission in the frontal cortex: i) Increased tissue levels of 5-HT and ii) increased extracellular 5-HT response to citalopram. Combined, these data strongly suggest that 5-HTP restores the sensitivity to SSRIs by increasing the brain 5-HT available for release. The frontal cortex could be involved, while it is less likely that the hippocampus is an anatomical substrate since 5-HTP decreased tissue 5-HT in this region.

In the tail suspension test, the decrease in immobility in mice after acute treatment with a compound is indicative of the compounds antidepressant potential following chronic treatment [3]. Thus, the 5-HTP restoration of the antidepressant-like response in NMRI mice indicates that 5-HTP may restore the clinical response to SSRIs in patient non-responders and/or enhance the clinical response in partial responders.

The invention claimed is:

1. A method of treatment or alleviation of a CNS disorder of a living animal body, including a human, which method comprises the step of administering to such a living animal body in need thereof, a therapeutically effective amount of a combination of
   (i) a slow-release formulation of 5-hydroxytryptophan or a pharmaceutically acceptable salt thereof wherein the 5-hydroxytryptophan or salt thereof is administered at a dosage of from 10 to 100 mg/kg/day, wherein the slow-release formulation of 5-hydroxytryptophan has a half-life of from 8 to 24 hours; and
   (ii) a selective serotonin reuptake inhibitor (SSRI) or a pharmaceutically acceptable salt thereof, wherein the CNS disorder is a disorder or condition selected from the group consisting of depressive disorders, bipolar disorders, anxiety disorders, obesity and pain.

2. The method according to claim 1, wherein the CNS disorder is a disorder or condition selected from the group consisting of depressive disorders, bipolar disorders, and anxiety disorders.

3. The method according to claim 1, wherein the CNS disorder is a disorder or condition selected from the group consisting of depression, interferon-induced depression, and depression resistant to re-uptake inhibitors.

4. The method according to claim 1, wherein the CNS disorder is depression resistant to re-uptake inhibitors.

5. The method according to claim 1, wherein the slow-release formulation of 5-hydroxytryptophan or a pharmaceutically acceptable salt thereof is a slow-release formulation of L-5-hydroxytryptophan or a pharmaceutically acceptable salt thereof.

6. The method according to claim 1, wherein the SSRI is selected from the group consisting of: citalopram, escitalopram, fluoxetine, fluvoxamine, paroxetine, sertraline, and pharmaceutically acceptable salts thereof.

7. The method according to claim 1, wherein the SSRI is fluoxetine or a pharmaceutically acceptable salt thereof.

8. The method according to claim 1, wherein the SSRI is citalopram, escitalopram, or a pharmaceutically acceptable salt thereof.

9. The method according to claim 1, wherein the slow-release formulation of 5-hydroxytryptophan has a half-life of from 12 to 24 hours.

10. A method of treating depression, wherein said depression is resistant to re-uptake inhibitors, in a human in need thereof, comprising administering in combination to said human in a treatment-effective amount:
    (i) a slow-release formulation of 5-hydroxytryptophan or a pharmaceutically acceptable salt thereof wherein the 5-hydroxytryptophan or salt thereof is administered at a dosage of from 10 to 100 mg/kg/day, wherein the slow-release formulation of 5-hydroxytryptophan has a half-life of from 8 to 24 hours; and
    (ii) a selective serotonin reuptake inhibitor (SSRI) or a pharmaceutically acceptable salt thereof.

11. The method of claim 10, wherein said administering is carried out simultaneously.

12. The method of claim 10, wherein said administering is carried out separately and sequentially.

13. The method of claim 10, wherein the slow-release formulation of 5-hydroxytryptophan or a pharmaceutically acceptable salt thereof is a slow-release formulation of L-5-hydroxytryptophan or a pharmaceutically acceptable salt thereof.

14. The method of claim 10, wherein the SSRI is selected from the group consisting of: citalopram, escitalopram, fluoxetine, fluvoxamine, paroxetine, sertraline, and pharmaceutically acceptable salts thereof.

15. The method of claim 10, wherein the serotonin-enhancing is fluoxetine or a pharmaceutically acceptable salt thereof.

16. The method of claim 10, wherein the SSRI is citalopram, escitalopram, or a pharmaceutically acceptable salt thereof.

17. The method of claim 10, wherein the slow-release formulation of 5-hydroxytryptophan has a half-life of from 12 to 24 hours.

18. A method of treating depression, wherein said depression is resistant to re-uptake inhibitors, in a human in need thereof, comprising administering in combination to said human in a treatment-effective amount:
    (i) a slow-release formulation of 5-hydroxytryptophan or a pharmaceutically acceptable salt thereof, and
    (ii) a selective serotonin reuptake inhibitor (SSRI) or a pharmaceutically acceptable salt thereof wherein the 5-hydroxytryptophan or salt thereof is administered at a dosage of from 10 to 100 mg/kg/day,
    wherein the slow-release formulation of 5-hydroxytryptophan has a half-life of from 8 to 24 hours, and
    wherein the slow-release formulation of 5-hydroxytryptophan is formulated for oral administration once or twice daily.

* * * * *

UNITED STATES PATENT AND TRADEMARK OFFICE
CERTIFICATE OF CORRECTION

PATENT NO. : 8,969,400 B2  
APPLICATION NO. : 12/680843  
DATED : March 3, 2015  
INVENTOR(S) : Jacobsen et al.

Page 1 of 1

It is certified that error appears in the above-identified patent and that said Letters Patent is hereby corrected as shown below:

In the Claims:
Column 12, Claim 10, Line 12: Please correct "salt thereof wherein"
to read -- salt thereof, wherein --

Column 12, Claim 15, Lines 31 and 32: Please correct "serotonin-enhancing"
to read -- SSRI --

Column 12, Claim 18, Line 46: Please correct "thereof wherein"
to read -- thereof, wherein --

Signed and Sealed this
Eleventh Day of August, 2015

Michelle K. Lee
*Director of the United States Patent and Trademark Office*